United States Patent [19]

Vandenbergh et al.

[11] Patent Number: 4,877,615

[45] Date of Patent: Oct. 31, 1989

[54] ANTIFUNGAL PRODUCT

[75] Inventors: Peter A. Vandenbergh, Sarasota; Blair S. Kunka, Bradenton, both of Fla.

[73] Assignee: Microlife Technics, Inc., Sarasota, Fla.

[21] Appl. No.: 248,438

[22] Filed: Sep. 23, 1988

[51] Int. Cl.[4] .................. A61K 35/00; C12P 13/08; C12P 7/56; C12P 1/04

[52] U.S. Cl. ..................... 424/115; 435/115; 435/139; 435/170; 435/171; 435/32; 435/68; 435/822; 514/2

[58] Field of Search ............. 435/171, 32, 68, 115, 435/822, 139, 170; 424/115; 514/2

[56] References Cited

U.S. PATENT DOCUMENTS

| | | | |
|---|---|---|---|
| 3,592,926 | 7/1971 | Ping Shu et al. | 435/822 |
| 4,452,895 | 6/1984 | Gonzalez | 435/822 |
| 4,508,738 | 4/1985 | Gonzalez | 435/822 |
| 4,524,136 | 6/1985 | Lee et al. | 435/139 |
| 4,716,153 | 12/1987 | Morishita et al. | 514/30 |

FOREIGN PATENT DOCUMENTS

| | | | |
|---|---|---|---|
| 0105194 | 6/1982 | Japan | 435/68 |
| 0093092 | 5/1984 | Japan | 435/68 |
| 1115100 | 6/1986 | Japan | 435/68 |

OTHER PUBLICATIONS

Abdel-Bar et al., J. Food Sci. 52: 411–415 (1987).
J. A. Angelo et al., J. Dairy Sci. 63: 52 (1980).
A. L. Branen et al., J. Food Sci. 40: 446–450 (1975).
Raccach, M. CRC Crit. Rev. Microbiol. 14: 291–309 (1987).
Dahiya et al., J. Dairy Sci. 51: 1568–1571 (1968).
Mundt et al., J. Bacteriol. 98: 938–942 (1969).
Yamaguchi, et al., Antimicrob. Agents. Chemother. 30: 705–712 (1986).
Vandenbergh et al., Appl. Environ. Microbiol. 42: 128–132 (1983).

Primary Examiner—Herbert J. Lilling
Assistant Examiner—Stephanie W. Zitomer
Attorney, Agent, or Firm—Ian C. McLeod

[57] ABSTRACT

A method for producing a novel antifungal product from a Pediococcus species is described. The preferred product (AFP) comprises a compound which contains valine and lactic acid and has a molecular weight of less than about 500 daltons. The product (AFP) is particularly useful in retarding fungal growth in foods and other materials in need thereof.

2 Claims, 2 Drawing Sheets

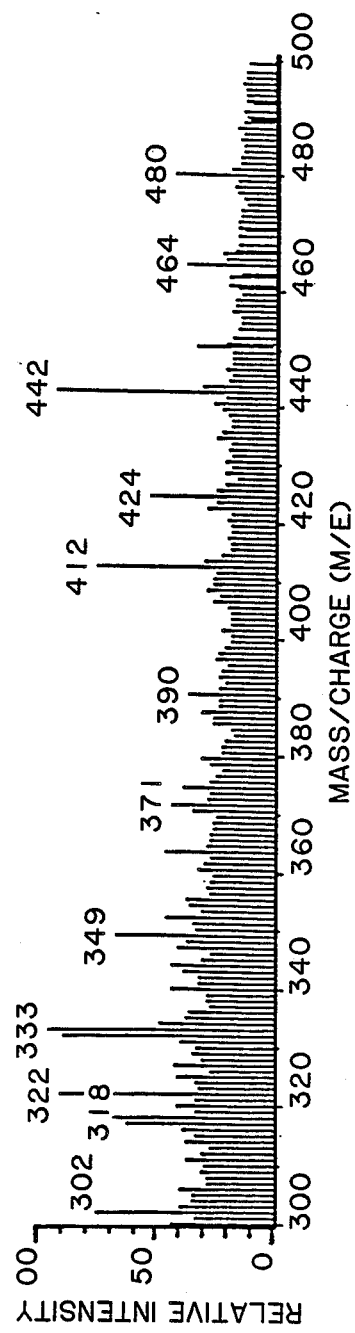

ANTIFUNGAL PRODUCT

BACKGROUND OF THE INVENTION

1. Field of the Invention

The present invention relates to an antifungal product (AFP) produced by Pediococcus species. In particular, the present invention relates to a method for producing the antifungal product (AFP) and to its use in preventing fungal (yeast and mold) growth in foods and other materials.

2. Prior Art

Antimicrobial compounds produced by lactic acid bacteria have been previously described (Abdel-Bar, N., N. D. Harris, and R. L. Rill., J. Food Sci. 52: 411–415 (1987); Angelo, J. A., Shahani, K. M., and A. D. Angelo, J. Dairy Sci. 63: 52 (1980); and Branen, A. L., Go, H. C., and R. P. Genske, J. Food Sci. 40: 446–450 (1975)). The compounds produced are usually bacteriocins, hydrogen peroxide and lactic acid (Raccach, M., CRC Crit. Rev. Microbiol. 14: 291–309 (1987); and Dahiya, R. S., and M. L. Speck, J. Dairy Sci. 51: 1568–1571 (1968)). The pediococci are considered lactic acid bacteria and produce lactic acid (Mundt, J. O., W. G. Beattie, and F. R. Wieland, J. Bacteriol. 98: 938–942 (1969)).

No antifungal products have been described as being produced by the pediococci. Previously antifungal products have been described as being produced by the soil Actinomycetes (Yamaguchi, H., K. Uchida, T. Hiratani, T. Hara, H. Fukuyasu, Y. Kazaro and S. Inouye, Antimicrob. Agents. Chemother, 30: 705–712 (1986)) and pseudomonads have previously been shown to indirectly inhibit fungal growth through siderophore production (Vandenbergh, P. A., C. F. Gonzalez, A. M. Wright, and B. S. Kunka, Appl. Environ. Microbiol. 42: 128–132 (1983)). These microorganisms are unrelated to pediococci.

In applications Ser. Nos. 794,468, filed Nov. 4, 1985 and 082,118, filed Aug. 6, 1987, which are assigned to a common assignee, antifungal products (FIC) from Lactobacillus sp. are described. These products (FIC) are mixtures which are chemically quite different from the products of the present invention.

OBJECTS

It is therefore an object of the present invention to provide a novel Pediococcus species derived metabolic product which inhibits fungi (yeast and mold) and which are referred to herein as "AFP" or "antifungal product". Further it is an object of the present invention to provide a method for producing the antifungal product as well as a method for using the product in foods and other materials. These and other objects will become increasingly apparent by reference to the following description and the drawings.

IN THE DRAWINGS

FIG. 2 shows the FAB mass spectrum of the partially purified product (AFP) of FIG. 1.

GENERAL DESCRIPTION

Figure 1:
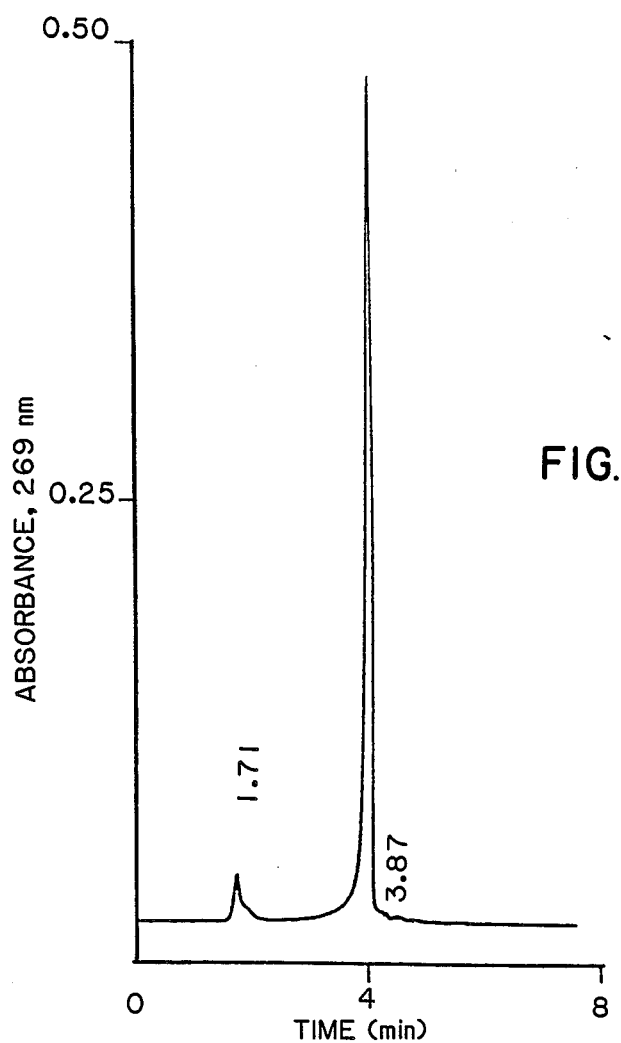
FIG. 1 shows a reverse phase HPLC chromatogram of the purified product (AFP) from *Pediococcus acidilactici* ATCC 25742.

The present invention relates to a method for producing an antifungal product which comprises: incubating live cells of a Pediococcus species in a growth medium for the cells to produce an isolable antifungal product in the growth medium which inhibits the growth of *Penicillium oxalicum* as an assay strain.

The present invention also relates to a method for producing an antifungal product (AFP) which comprises: incubating live cells of a Pediococcus species in a growth medium for the cells so as to produce an isolable amount of the product (AFP) in the growth medium, wherein the product (AFP) produced in the growth medium or separated from the growth medium inhibits the growth of *Penicillium oxalicum*, as an assay strain and wherein the product (AFP) is a compound containing valine and lactic acid having a molecular weight of less than about 500 daltons.

The present invention further relates to a method for inhibiting fungal growth in a material in need thereof which comprises: adding to the material an antifungal product produced by a method which comprises incubating live cells of a Pediococcus species in a growth medium for the cells to produce an isolable amount of the antifungal product in the growth medium which inhibits the growth of *Penicillium oxalicum* as an assay strain.

The present invention also relates to an antifungal product (AFP) produced by a Pediococcus sp which comprises a compound containing lactic acid and valine having a molecular weight of less than about 500 daltons, which is digested by protease and which inhibits *Penicillium oxalicum*, as an assay strain, in an optimal pH range between about pH 1 and 5.

The present invention also relates to a method for producing an antifungal product (AFP) which comprises: incubating live cells of a Pediococcus species in a growth medium for the cells containing growth factors present in corn steep liquor, cysteine, garlic extract, milk digest, yeast extract, milk, egg or soy enzymatic digest or milk, egg or soy hydrolyzate which induce the formation of the product (AFP), containing a protein source and containing a carbon source, so as to produce the product (AFP) in the growth medium; and treating the growth medium which has been incubated so as to produce the product (AFP) with or without the live cells, wherein the product (AFP) inhibits the growth of *Penicillium oxalicum* spores as an assay strain in an assay with the product (AFP) and the *Penicillium oxalicum* spores mixed and wherein the product (AFP) comprises a compound containing valine and lactic acid having a molecular weight of less than about 500 daltons.

The preferred antifungal product (AFP) is produced by *Pediococcus acidilactici* ATCC 25742. It is on deposit with the American Type Culture Collection, Beltsville, Md. Any Pediococcus strain, whether naturally occurring or genetically engineered, with genetic material (in chromosomes or plasmids) encoding for the antifungal product can be used to produce the product. *Pediococcus acidilactici* ATCC 25742 appears to be the most effective naturally occurring (non-genetically engineered) source of the preferred product (AFP).

Various growth media for Pediococcus can be used. The medium must promote growth of cells and production of the antifungal product (AFP). The medium must contain protein and a carbon source to promote growth. The medium includes growth factors which promote the production of the product (AFP). Growth factors are cornsteep liquor, cysteine, garlic extract, milk digest, yeast extract, milk, egg or soy enzymatic digest or milk, egg or soy hydrolyzate.

Proteinaceous or amino acid materials from natural sources are used in the growth medium. Thus protein sources such as milk, whey, yeast, yeast extract or protein digest can be used. The carbon source can include fructose, sucrose, dextrose, or molasses. Minerals which facilitate growth of the cells, such as manganese and magnesium salts are available in cornsteep liquor or can be added as pure salts. Preferably buffers such as alkali metal phosphates are used to maintain the pH. Preferably the cells are grown at a temperature between 10° and 50° C. Numerous variations of the nutrient medium and growth conditions will occur to those skilled in the art.

After growth of the cells, the growth medium preferably is processed to eliminate most of the live cells and then the growth medium is concentrated or the antifungal product (AFP) is separated from the growth medium. The antifungal product can be dried, lyophilized, refrigerated or frozen prior to use. The preferred process for producing the product in a relatively unconcentrated form includes spray drying the growth medium after the antifungal product is produced in the medium. All of these methods are well known to those skilled in the art.

The product can be separated from the growth medium by ultrafiltration, which is preferred, and by chromatographic methods including molecular sieve, ion exchange and high pressure liquid chromatography methods well known to those skilled in the art. Impurities can be removed from the product (AFP) using molecular sieves, ultrafiltration, reverse osmosis and other microporous filter means. Various organic solvents can also be used to extract the product from the growth medium, such as lower alkyl alcohols and esters. Preferably n-butanol isopropanol, acetone, ethyl acetate or ethanol and combinations with water are used. Essentially any chemical and/or mechanical method can be used for the separation. The preferred product (AFP) comprises substantially a peptide which has a molecular weight of less than about 500 daltons, a pH optimum of 3 and is not sensitive to exposure to a temperature of 100° C. for 60 minutes. The product was purified through the use of butanol extraction and HPLC. Chromatography was performed using reverse phase HPLC on a C8 preparative column. Amino acid analysis demonstrated the presence of the amino acid valine in the purified fraction. Mass spectral analysis demonstrated a molecular weight for the peptide of less than about 500 and above about 400 daltons. Substantial amounts of lactic acid can be present in the particular purified product (AFP)

The product (AFP) inhibited the following representative fungi: *Aspergillus flavus, A. niger, A. terreus, Chaetomium globosum,* Cladosporium sp., *Fusarium solani, Monilinia fructicola, Penicillium oxalicum,* Penicillium sp, Trichoderma sp and *Saccharomyces cerevisiae.*

As used herein, the term "material" means any surface in need of treatment by the product. The term "material" includes living and non-living surfaces. The antifungal product (AFP) is preferably used in foods in an amount which inhibits *P. oxalicum* as the assay strain for at least 72 hours. The term "inhibition" means that the assay strain does not grow as effectively as without the product (AFP). The amount of product (AFP) used depends upon the number of fungal cells in the material to be treated.

Any food can be preserved by the method of the present invention especially pet foods; carbonated beverages; Cottage cheese; yogurt; margarine; bread; grains and nuts. Because the product (AFP) is effective in a broad pH range, the product (AFP) is especially useful in any food treated by the method of the present invention. The antifungal product is particularly useful in fermented foods, processed foods and preserved foods which are prone to fungal spoilage. Other food applications include silage, corn and peanut mold treatment to prevent aflatoxin contamination by mold. Various non-food materials, such as paper, fabrics and plastic materials, can be treated with the product (AFP). The product (AFP) can be used to prevent infection in living tissue either in tissue culture or in an animal, particularly in mammals. Topical application of the product (AFP) to mammals either internal or external is preferred. Soaps, shampoos, hair and skin conditioners, and cosmetics can be combined with the product (AFP).

SPECIFIC DESCRIPTION

Summary of Examples

The following Examples show the isolation of and testing of the product (AFP) from *Pediococcus acidilactici* ATCC 25742 which is preferred. Product (AFP) having similar antifungal characteristics to the preferred product (AFP) are obtained from other strains of Pediococcus as shown hereinafter in Example 1.

EXAMPLE 1

Various isolates of Pediococcus sp. were maintained as stock cultures in liquid nitrogen and propagated on MRS TM media (Difco, Detroit, MI).

The Pediococci sp. were cultivated for 18 hours on MRS TM agar at 35° C. in 1.0 cm circular patches on the surface of the agar. Each plate was then overlayed with 8 ml of MRS TM soft agar containing $10^5$ spores/ml of *Penicillium oxalicum*. Fungal spore suspensions were prepared in sterile distilled water and adjusted to an absorbence of 0.1 at 530 nm. After 48 hours, the inhibitory zone surrounding each 1.0 cm circular cultural patch was examined. The results are shown in Table 1.

TABLE 1

**FUNGAL INHIBITORY ACTIVITY OF *PEDIOCOCCI SP.***

| Strain | | Inhibitory zone size (mm) | Origin |
|---|---|---|---|
| Pediococcus acidilactici | ATCC 25740 | 3.0 | ATCC[a] |
| | ATCC 25741 | 4.5 | ATCC |
| | ATCC 8081 | 3.0 | ATCC |
| | ATCC 25742 | 5.5 | ATCC |
| | ATCC 25743 | 4.0 | ATCC |
| | ATCC 8042-2 | 4.0 | ATCC |
| | NRRL-B-18050 | 1.0 | NRRL[b] |
| Pediococcus damnosus | ATCC 19371 | 1.5 | ATCC |
| Pediococcus dextrinicus | ATCC 33087 | 0.0 | ATCC |
| Pediococcus halophilis | ATCC 33315 | 0.0 | ATCC |
| Pediococcus parvulus | ATCC 19371 | 1.0 | ATCC |
| Pediococcus pentosaceus | ATCC 10791 | 4.0 | ATCC |
| | ATCC 25744 | 3.5 | ATCC |
| | ATCC 25745 | 3.0 | ATCC |
| | ATCC 33316 | 2.0 | ATCC |
| Pediococcus urinaeequi | ATCC 29723 | 0.0 | ATCC |

[a]American Type Culture Collection, Rockville, MD.
[b]Northern Regional Research Laboratory, Peoria, Illinois.

As can be seen, *Pediococcus acidilactici* ATCC 25742 is the best producer of an antifungal product (AFP). *Pediococcus pentosaceus* also produced good amounts of the antifungal product (AFP).

EXAMPLE 2

This Example shows nutritional requirements of the preferred strain in various growth media. *Pediococcus acidilactici* ATCC 25742 was grown for 18 hours at 35° C. in 100 ml of MRS ™ broth supplemented with different nutritional additives. After 18 hours the culture was then centrifuged at 10,000×g for 20 minutes at 4° C. and the supernatant was then subjected to further extractions. The supernatant was concentrated on a flash evaporator to dryness and resuspended in 10 ml of distilled water. This was mixed with 100 ml n-butanol. The water-butanol mixture was then placed in a separatory funnel and allowed to equilibrate for 60 minutes at 25° C. The butanol layer was then extracted and concentrated on the flash evaporator to dryness. The residue was then resuspended in 5 ml distilled water, washed and concentrated. The washed residue was then resuspended in 5 ml of distilled water. The washed resuspended residue (1 ml) was then mixed with 8 ml of MRS ™ soft agar and $10^5$ spores/ml of *Penicillium oxalicum* and overlayed onto the surface of MRS ™ agar and incubated at 25° C. for 72 hours. The results are shown in Tables 2 and 3.

TABLE 2

NUTRITIONAL REQUIREMENTS OF ATCC 25742

| MEDIUM | INCUBATION TIME | | |
|---|---|---|---|
| | 24 h | 48 h | 72 h[a] |
| Control uninoculated MRS ™ broth (Difco ™, Detroit Michigan) | +1 | +4 | +4 |
| MRS ™ broth (Difco ™) Control | − | +1 | +2 |
| MRS ™ broth (Difco ™) supplemented with 1% yeast extract (Oxoid) | − | − | +1 |
| MRS ™ broth (Difco ™) supplemented with 1% yeast extract (Tureen) | − | +/− | +1 |
| MRS ™ broth (Difco ™) supplemented with 0.01% cysteine | − | +1 | +2 |
| MRS ™ broth (Difco ™) supplemented with 1.0% cysteine | − | − | +1 |
| MRS ™ broth (Difco ™) supplemented with 1.0% whey protein concentrate | − | +1 | +1 |
| MRS ™ broth (Difco ™) supplemented with 1.0% Albutone ™ (enzymatic digest of egg albumen) (Kraft ™, Sheffield Products, Kraft, Inc., Norwich, NY) | − | − | +1 |
| MRS ™ broth (Difco ™) supplemented with 1.0% N—Z—Amine type EKC ™ (enzymatic digest of casein) (Kraft ™, Sheffield Products, Kraft, Inc., Norwich, NY) | − | +1 | +2 |
| MRS ™ broth (Difco ™) supplemented with 1.0% N—Z—Amine type AS ™ (enzymatic digest of casein high solubility) (Kraft ™, Sheffield Products, Kraft, Inc., Norwich, NY) | − | +1 | +2 |
| MRS ™ broth (Difco ™) supplemented with 1.0% Edamin S ™ (enzymatic digest of lactalbumin (Kraft ™, Sheffield Products, Kraft, Inc., Norwich, NY) | − | − | − |
| MRS ™ broth (Difco ™) supplemented with 1.0% Hy Case | − | +1 | +2 |
| MRS ™ broth (Difco ™) supplemented with 1.0% Hy Soy | − | +1 | +2 |

[a] − = No fungal colonies present.
+1 = Fungal colonies present at greater than 1000 per plate.
+2 = Confluent white lawn of mycelium.
+3 = Confluent mycelial lawn piled in mass.
+4 = Confluent mycelial lawn with green pigmentation.

TABLE 3

NUTRITIONAL SUPPLEMENTS TO A CORNSTEEP BASED MEDIUM EFFECTS ON ANTIFUNGAL ACTIVITY PRODUCED BY ATCC 25742

| MEDIUM | INCUBATION TIME | | |
|---|---|---|---|
| | 24 h | 48 h | 74 h[a] |
| 8% Cornsteep, 3% yeast extract, 5% dextrose, 1.2% Hy Soy ™, and 1.2% Hy Case ™ | − | + | +2 |
| 8% Cornsteep, 3% yeast extract, 5% dextrose, 1.2% Hy Soy ™, 1.2% Hy Case ™ supplemented with 1% molasses | + | +2 | +3 |
| 8% Cornsteep, 3% yeast extract, 5% dextrose, 1.2% Hy Soy ™, 1.2% Hy Case ™ supplemented with 1.0% cysteine | − | +/− | +2 |
| 8% Cornsteep, 3% yeast extract, 5% dextrose, 1.2% Hy Soy ™, 1.2% Hy Case ™ supplemented with 1% garlic extract | − | + | +2 |
| 8% Cornsteep, 3% yeast extract, 5% dextrose, 1.2% Hy Soy ™, 1.2% Hy Case ™ supplemented with 1% Edamin S. ™ | − | +/− | + |
| 8% Cornsteep, 3% yeast extract, 5% dextrose, 1.2% Hy Soy ™, 1.2% Hy Case ™ supplemented with 1% Albutone | − | +/− | +2 | a − = No fungal colonies present.
+1 = Fungal colonies present at greater than 1000 per plate.
+2 = Confluent white lawn of mycelium.
+3 = Confluent mycelial lawn piled in mass.
+4 = Confluent mycelial lawn with green pigmentation.

In Table 2, the enzymatic digest of lactalbumin produced the greatest stimulatory effect on the production of the product (AFP). As shown in Table 3, a commercial medium was prepared using cornsteep, yeast extract and dextrose with various supplements. The enzymatic digest of lactalbumin produced the greatest stimulatory effect on production of the product (AFP).

EXAMPLE 3

This Example shows the inhibitory spectrum of the product (AFP) from *Pediococcus acidilactici* ATCC 25742 against various fungal species. *Pediococcus acidilactici* ATCC 25742 was grown for 18 hours at 35° C. in one liter of MRS ™ broth supplemented with 1.0% Edamin S ™ (Kraft, Norwich, NY). The culture was centrifuged at 10,000×g at 4° C. for 20 minutes. The supernatant was then concentrated using a flash evaporator and concentrated to 100 ml. This material was then extracted with 900 ml of n-butanol, placed in a separatory funnel and equilibrated for 60 minutes at 25° C. The butanol layer was then concentrated on the flash evaporator and washed and resuspended in 10 ml of distilled water. The washed resuspended residue (1 ml) was the assayed against various fungi at a concentration of $10^5$ spores/ml. Fungal spore suspensions were prepared in sterile distilled water and adjusted to an absorbance of 0.1 at 530 nm. The results are shown in Table 4.

TABLE 4
INHIBITORY SPECTRUM OF *PEDIOCOCCUS ACIDILACTICI* ATCC 25742 AGAINST VARIOUS FUNGAL SPECIES

| Fungal Species | ATCC 25742 |
| --- | --- |
| *Aspergillus flavus* | + |
| *Aspergillus niger* | + |
| *Aspergillus terreus* | + |
| *Candida albicans* | − |
| *Chaetomium globosum* | + |
| *Cladosporium sp.* | + |
| *Fusarium solani* | + |
| *Geotrichum candidum* | − |
| *Monilinia fructicola* | + |
| *Mucor mucedo* | − |
| *Penicillium oxalicum* | + |
| *Penicillium sp.* | + |
| *Saccharomyces cerevisiae* | − |
| *Trichoderma sp.* | + |
| *Paecilomyces sp.* | − |

+ Fungal growth was inhibited
− Fungal growth was not inhibited

The product (AFP) was able to inhibit *Aspergillus flavus, A. niger, A. terreus, Chaetomium globosum,* Cladosporium sp., *Fusarium solani, Monilinia fructicola, Penicillium oxalicum,* Trichodermia sp, Penicillium sp. and *Saccharomyces cerevisiae*.

EXAMPLE 4

The following example shows the purification procedure for and characterization of the preferred product (AFP). *Pediococcus acidilactici* ATCC 25742 was inoculated into 1.0 liter of MRS TM broth supplemented with 1.0% Edamin S TM. The culture was incubated for 18 hours at 35° C. The material was then processed in the following manner:

Step 1: Cells and medium were centrifuged at 10,000×g for 20 minutes at 4° C. The cells were discarded and the supernatant was concentrated using a flash evaporator to 100 ml.

Step 2: The concentrated supernatant was then mixed with 900 ml of n-butanol placed into a separatory funnel and allowed to equilibrate at 25° C. for 60 minutes.

Step 3: The butanol layer was extracted and concentrated to dryness using the flash evaporator. The residue was redissolved in 10 ml of distilled water washed concentrated and redissolved in 10 ml of distilled water.

Step 4: The washed resuspended residue was then passed through a series of Sep-Pak TM C-18 cartridges (Waters Associates, Milford, MA) until the residue was a light amber color.

Step 5: The Sep-Pak TM preparation (400 ul) was loaded onto a Econosil C-8 TM (250×10 mm, 10 um particles, from Alltech Associates, Deerfield, Il) preparative column. The column was eluted using water as the mobile phase at a rate of 2.0 ml/min. Column temperature was maintained at 80° C. The elutant was monitored at 269 nm and 1.0 ml fractions were collected.

The fractions were assayed in a sterile tube using 50 ul of assay material was mixed with 50 ul of *Penicillium oxalicum* ($10^5$ spores/ml concentration standardized at A 530 nm to 0.1) and combined with 400 ul of MRS TM soft agar.

Samples of the butanol extracted, concentrated material were adjusted to pH values in a range from 1.0 to 12.0 using 1.0N HCl or 1.0N NaOH. Antifungal activities were then measured after storage at 4° C. for 24 hours. One ml samples of the butanol extracted, concentrated material was incubated at various temperatures 25°, 37°, 60°, 100° and 121° C. for various time intervals. Antifungal activities were then measured to determine whether there was any degradation.

Purification of the antifungal product (AFP) was accomplished using butanol extraction and purification using a C-8 preparative column. Fractions were collected and assayed for antifungal activity.

Preparative HPLC chromatograms of partially purified product (AFP) resulted in antifungal activity in the fractions collected between 9 and 9.5 minutes. Subsequent analysis of the active fractions by analytical HPLC demonstrated a single peak as shown in FIG. 1.

Amino acid profiles for purified fractions were obtained using a modification of the PICO-TAG TM system (Waters Associates, Milford, MA). The method involves sample hydrolysis followed by derivatization with phenylisothiocyanate and subsequent analysis by HPLC (Mundt, J. O., W. G. Beattie, and F. R. Wieland, J. Bacteriol. 98: 938–942 (1969)). Amino acids were identified by comparing the retention times of a known standard to that of the active fraction hydrolyzate.

Mass spectra were obtained using a VG Micromass 7070 EQ magnetic sector mass spectrometer. Ionization was accomplished using an Ion Tech TM FAB gun accelerating neutral xenon atoms to 8 KV. The sample matrix was dithiothreitol:dithioerythritol (3:1).

Prominent mass peaks were observed as shown in FIG. 2 at M/E=442 which represents the molecular ion +1, M/E=464 which represents the molecular ion +23 for sodium and M/E=480 which represents the molecular ion +39 for potassium. The product (AFP) contained valine and lactic acid.

EXAMPLE 5

The effect of enzymes on the antifungal activity of the product (AFP) of Example 4 was determined using various enzymes obtained from Sigma Chemical Co., St. Louis, MO. The enzymes included protease, lysozyme, lipase, DNase and RNase. Stock solutions (10 mg/ml) of each of the enzymes in their appropriate buffers were prepared. Partially purified antifungal product (AFP) was incubated with each stock enzyme for 60 minutes at the appropriate temperature. Following the incubation, each preparation was then boiled at 100° C. for 3 minutes to inactivate the enzymes. The antifungal product (AFP) was then assayed for activity.

The product (AFP) was sensitive to protease. The antifungal activity was not affected by lipase, lysozyme, DNase, RNase or heating to 100° C. for 60 minutes. Autoclaving at 121° C. for 15 minutes at 15 lbs/in² did not affect activity. Activity was observed to be most stable at pH 1 to 5 with a loss in activity above a pH of about 5. Dialysis experiments using various membranes demonstrated the molecular size of the antifungal product (AFP) to be less than 1000 daltons.

EXAMPLE 6

The example shows membrane ultrafiltration of the product (AFP). *Pediococcus acidilactici* ATCC 25742 was grown in 1 liter of MRS TM broth supplemented with 1% yeast extract at 35° C. for 18 hours.

The cells were centrifuged at 10,000×g for 15 minutes at 4° C. The supernatant was collected and filter sterilized through a 0.22 micrometer filter.

The filter sterilized supernatant was then placed in an Amicon TM Model 8200 Ultrafiltration cell (Division of W. R. Grace Co., Danvers, MA). The supernatant was then filtered through two Diaflo ™ ultrafiltration membranes, YM10 and YC05. Their molecular weight cutoffs are 10,000 and 500 daltons, respectively. Antifungal activity assays were performed on the filtrates from the membrane ultrafiltration.

Results indicated that the antifungal activity was associated with the filtrate from both passages, YM10 and YC05. The starting volume was 1000 ml and the final volume was 950 ml. This showed that the antifungal product had a molecular weight of less than 500 daltons.

EXAMPLE 7

The example shows the concentration of the ultrafiltrated product (AFP). The product (AFP) was prepared using the Amicon ™ Model 8200 ultrafiltration cell. The supernatant was filtered through a YM10 Diaflo ™ and a YC05 Diaflo ™ ultrafiltration membrane. The filtrate from the YC05 membrane was then subjected to 10 fold concentration using flash evaporation or using lyophilization.

The activity of the product (AFP) produced was monitored using a tube assay: 50 ul of AFP material, 50 ul of fungal spores (P. oxalicum) A 530 nm=0.1 and 400 ul of MRS ™ soft agar. The (AFP) product was assayed undiluted and serially diluted 1:1 and 1:2. The flash evaporated YC05 filtrate product (AFP) showed antifungal activity in the undiluted and 1:1 diluted preparations. The lyophilized YC05 filtrate product (AFP) showed antifungal activity in the undiluted, 1:1 and 1:2 preparations.

The results indicated that the product AFP can be concentrated using lyophilization or flash evaporation but with some loss of activity.

EXAMPLE 8

The product (AFP) was added to commercial spaghetti sauce (pH 4.3) and examined for its ability to inhibit the growth of P. oxalicum. The spaghetti sauce contained the following ingredients: crushed tomatoes, soybean oil, salt, olive oil, romano cheese, dehydrated garlic spice, and natural flavoring. Spaghetti sauce (20 g) was placed in a sterile petri dish, and P. oxalicum was added to result in a final concentration of $2.5 \times 10^3$ spores/gm of spaghetti sauce. AFP (1 ml) made as in Example 3 was mixed with the sauce in the experimental plate. The petri dishes were then incubated at 30° C. for several days. The growth of P. oxalicum was observed after 48 hours in the control (no AFP added), whereas the experimental that contained AFP did not have observable fungal growth even after 120 hours.

EXAMPLE 9

The product (AFP) was added to yogurt (ph 4.1) and examined for its ability to inhibit the growth of P. oxalicum. The yogurt contained the following ingredients: cultured skim milk, gelatin and modified food starch and live yogurt cultures. Yogurt (20 g) was placed in a sterile petri dish, and P. oxalicum was added to result in a final concentration of $2.5 \times 10^3$ spores/gm of yogurt. AFP (1 ml) made as in Example 3 was mixed with the yogurt in the experimental plate. The plates were incubated at 30° C. for several days. The growth of P. oxalicum was observed after 96 hours in the control (no AFP added), whereas the experimental plate that contained AFP did not have observable fungal growth even after 144 hours.

EXAMPLE 10

The product (AFP) was added to soft margarine (pH 5.0) and examined for its ability to inhibit the growth of P. oxalicum. The soft margarine contained the following ingredients: liquid soybean oil, partially hydrogenated soybean oil, water, salt, whey, vegetable mono and diglycerides, soybean lecithin, sodium benzoate and citric acid. Soft margarine (20 g) was placed in a sterile petri dish, and P. oxalicum was added to result in a final concentration of $2.5 \times 10^3$ spores/gm of margarine. AFP (1 ml) made as in Example 3 was mixed with the margarine in the experimental plate. The petri dishes were then incubated at 30° C. for several days. The growth of P. oxalicum was observed after 96 hours in the control (no AFP added), whereas the experimental plate that contained AFP did not have observable fungal growth even after 144 hours.

EXAMPLE 11

The product (AFP) was added to cheese slices and examined for its ability to inhibit the growth of P. oxalicum. The cheese contained the following ingredients: milk, cheese culture, salt, enzymes, calcium chloride, water, skim milk cheese, whey, cream, sodium citrate, salt and sorbic acid. Cheese slices (20 g) were placed in a sterile petri dish, and P. oxalicum was added to result in a final concentration of $2.5 \times 10^3$ spores/gm of cheese slices. AFP (1 ml) made as in Example 3 was mixed with the cheese slices in the experimental plate. The petri dishes were then incubated at 30° C. for several days. The growth of P. oxalicum was observed after 48 hours in the control (no AFP added), whereas the experimental that contained AFP did not have observable fungal growth even after 120 hours.

EXAMPLE 12

The product (AFP) was added to Cottage cheese (pH 5.1) and examined for its ability to inhibit the growth of P. oxalicum. The Cottage cheese contained the following ingredients: cultured skim milk, milk cream, salt, stabilizer (guar gum, locust bean gum and carrogeenan), lactic acid and phosphoric acid. Cottage cheese (20 g) was placed in a sterile petri dish, and P. oxalicum was added to result in a final concentration of $2.5 \times 10^3$ spores/gm of Cottage cheese. AFP (1 ml) made as in Example 3 was mixed with the experimental plate. The petri dishes were then incubated at 30° C. for several days. The growth of P. oxalicum was observed after 72 hours in the control (no AFP added), whereas the experimental plate that contained AFP did not have observable fungal growth even after 120 hours.

EXAMPLE 13

The product (AFP) was added to pepperoni slices (pH 4.8) and examined for its ability to inhibit the growth of P. oxalicum. The pepperoni contained the following ingredients: pork, beef, salt, water, dextrose, natural spices, lactic acid, starter culture, oleoresin, paprika, dehydrated garlic, sodium nitrite, BHA, BHT and citric acid. Pepperoni slices (20 g) were placed in a sterile petri dish, and P. oxalicum was added to result in a final concentration of $2.5 \times 10^3$ spores/gm of pepperoni slices. AFP (1 ml) made as in Example 3 was mixed with the pepperoni slices in the experimental plate. The petri dishes were then incubated at 30° C. for several days. The growth of P. oxalicum was observed after 36 hours in the control (no AFP added), whereas the experimental that contained AFP did not have observable fungal growth even after 144 hours.

It is intended that the foregoing description be only illustrative of the present invention and that the invention be limited by the hereinafter appended claims.

We claim:

1. An antifungal product (AFP) produced by *Pediococcus acidilactici* ATCC 25742 which comprises a compound consisting of lactic acid and valine having a molecular weight of above 400 daltons and less than about 500 daltons, which is digested by protease, and inhibits *Penicillium oxalicum* as an assay strain in an optimal pH range between about pH 1 and 5 and which has a FAB mass spectrum as shown in FIG. 2.

2. A product (AFP) which is a compound consisting of valine and lactic acid having a high pressure liquid chromatographic spectrum in water as shown in FIG. 1 and having a FAB mass spectrum as shown in FIG. 2.

* * * * *